United States Patent
Young et al.

(10) Patent No.: US 12,210,022 B2
(45) Date of Patent: Jan. 28, 2025

(54) URINE MARKERS AND FORMULA FOR DIAGNOSING OVERACTIVE BLADDER DISORDER

(71) Applicant: University of Portsmouth Higher Education Corporation, Portsmouth (GB)

(72) Inventors: John S. Young, Portsmouth (GB); Sepinoud Firouzmand, Portsmouth (GB)

(73) Assignee: UNIVERSITY OF PORTSMOUTH HIGHER EDUCATION CORPORATION, Portsmouth (GB)

( * ) Notice: Subject to any disclaimer, the term of this patent is extended or adjusted under 35 U.S.C. 154(b) by 1171 days.

(21) Appl. No.: 16/970,327

(22) PCT Filed: Feb. 18, 2019

(86) PCT No.: PCT/GB2019/050416
§ 371 (c)(1),
(2) Date: Aug. 14, 2020

(87) PCT Pub. No.: WO2019/158937
PCT Pub. Date: Aug. 22, 2019

(65) Prior Publication Data
US 2021/0080473 A1 Mar. 18, 2021

(30) Foreign Application Priority Data
Feb. 19, 2018 (GB) ..................................... 1802653

(51) Int. Cl.
*G01N 33/68* (2006.01)
*G16B 40/00* (2019.01)

(52) U.S. Cl.
CPC ......... *G01N 33/6893* (2013.01); *G16B 40/00* (2019.02); *G01N 2333/523* (2013.01); *G01N 2333/5409* (2013.01); *G01N 2800/341* (2013.01)

(58) Field of Classification Search
None
See application file for complete search history.

(56) References Cited

PUBLICATIONS

Alkis et al. "The use of biomarkers in the diagnosis and treatment of overactive bladder: Can we predict the patients who will be resistant to treatment?" Neurology and Urodynamics, (First published Dec. 10, 2015), vol. 36, Issue 2, pp. 390-393. (Year: 2017).*
Rovner et al. "Chapter 2: Diagnosis of Overactive Bladder." In: Contemporary Pharmacotherapy of Overactive Bladder, L. Cox, E.S. Rovner (eds.), Springer, pp. 13-25, https://doi.org/10.1007/978-3-319-97265-7_2. (Year: 2019).*
ISA; International Search Report and Written Opinion dated May 2, 2019 in Application No. PCT/GB2019/050416.
UKIPO; Search Report dated Oct. 30, 2018 in GB Application No. 1802654.4.
Pennycuff et al. "Current Concepts in Urinary Biomarkers for Overactive Bladder: What is the Evidence?", Current Bladder Dysfunction Reports, Springer US, Boston, vol. 12, No. 4, Jun. 20, 2017, pp. 260-267.
Silva-Ramos et al. "Overactive bladder syndrome: Evidence that urinary ATP is a dynamic biomarker of detrusor pveractivity", Autonomic Neuroscience: Basic and Clinical, vol. 177(1), 2013, pp. 21-22.
Tyagi et al., "Urine cytokines suggest an inflammatory response in the overactive bladder: a pilot study", International Urology and Nephrology, vol. 42 (3), 2009, pp. 629-635.

* cited by examiner

*Primary Examiner* — John S Brusca
*Assistant Examiner* — Steven W. Bailey
(74) *Attorney, Agent, or Firm* — Shell & Wilmer L.L.P.

(57) ABSTRACT

The present invention relates to a method of diagnosing over active bladder disorder (OAB), the method comprising: measuring the concentrations of adenosine triphosphate (ATP), acetylcholine (ACh), nitrite, monocyte chemoattractant protein 1 (MCP-1) and interleukin 5 (IL-5) in a sample obtained from a subject; normalising the concentrations to the concentration of creatinine (Cr) in the sample; range standardising the normalised concentrations and subject's age to the following values: Age to 120 years old; ATP/Cr to 0.000001 mole/mg×dl$^{-1}$; ACh/Cr to 0.1 mole/mg×dl$^{-1}$; Nitrite to 200 nM/mg×dl$^{-1}$; MCP-1/Cr to 100 pg×ml$^{-1}$/mg×dl$^{-1}$; IL-5/Cr 100 pg×ml-mg×dl$^{-1}$; applying the normalised and range standardised concentrations to the following formula: Logit (p)=−1.738±1.404±4.985±2.914×subject's age+3315.959±5435.254×[ATP]/[Cr]+(−25204.194±20268.337)×[ACh]/[Cr]+26.799±32.967×[nitrite]/[Cr]+6.755±25.132 [MCP-1]/[Cr]+(−61.838±148.740) [IL-5]/[Cr] and calculating Logit; wherein a Logit value above a predetermined threshold indicates that the subject has OAB. Methods for monitoring the progression of OAB using the method, kits for use in the method and computer systems and programs configured to execute the method are also provided.

12 Claims, 8 Drawing Sheets

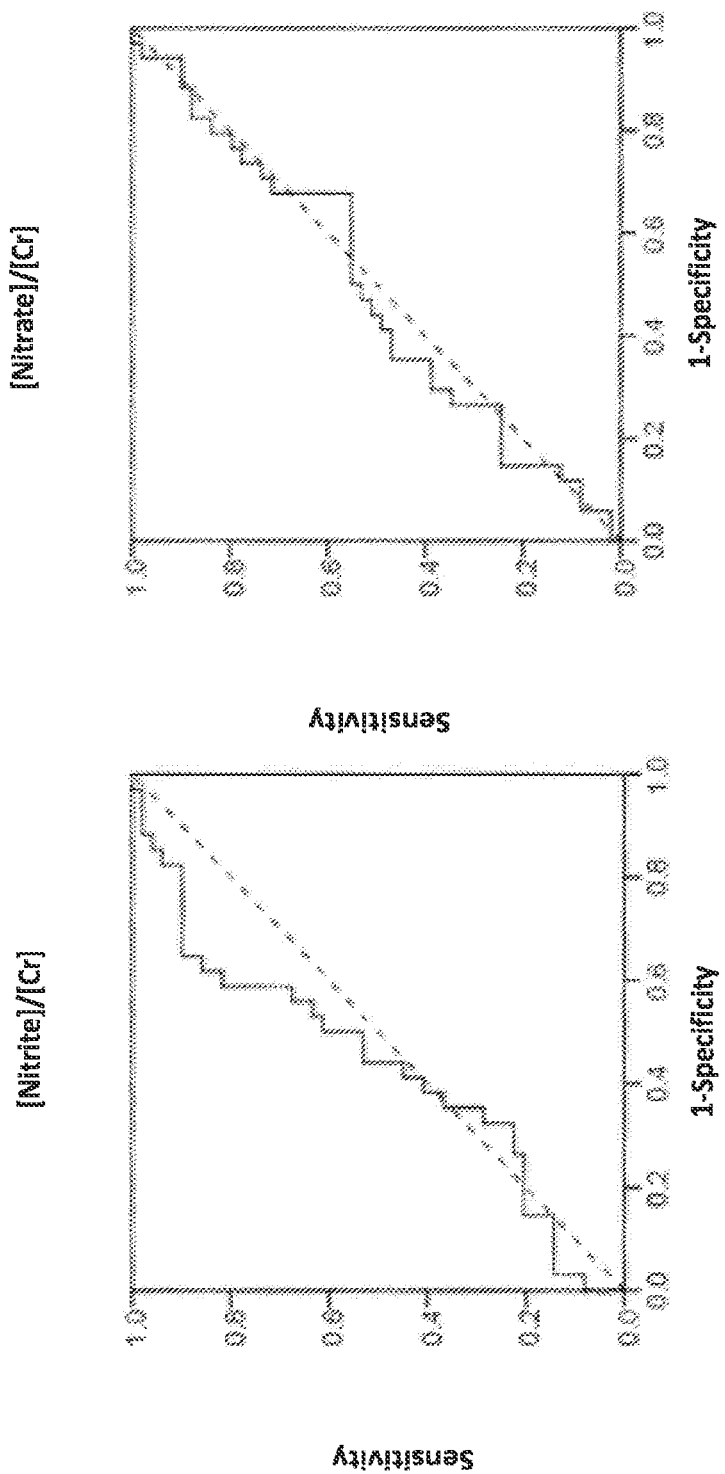

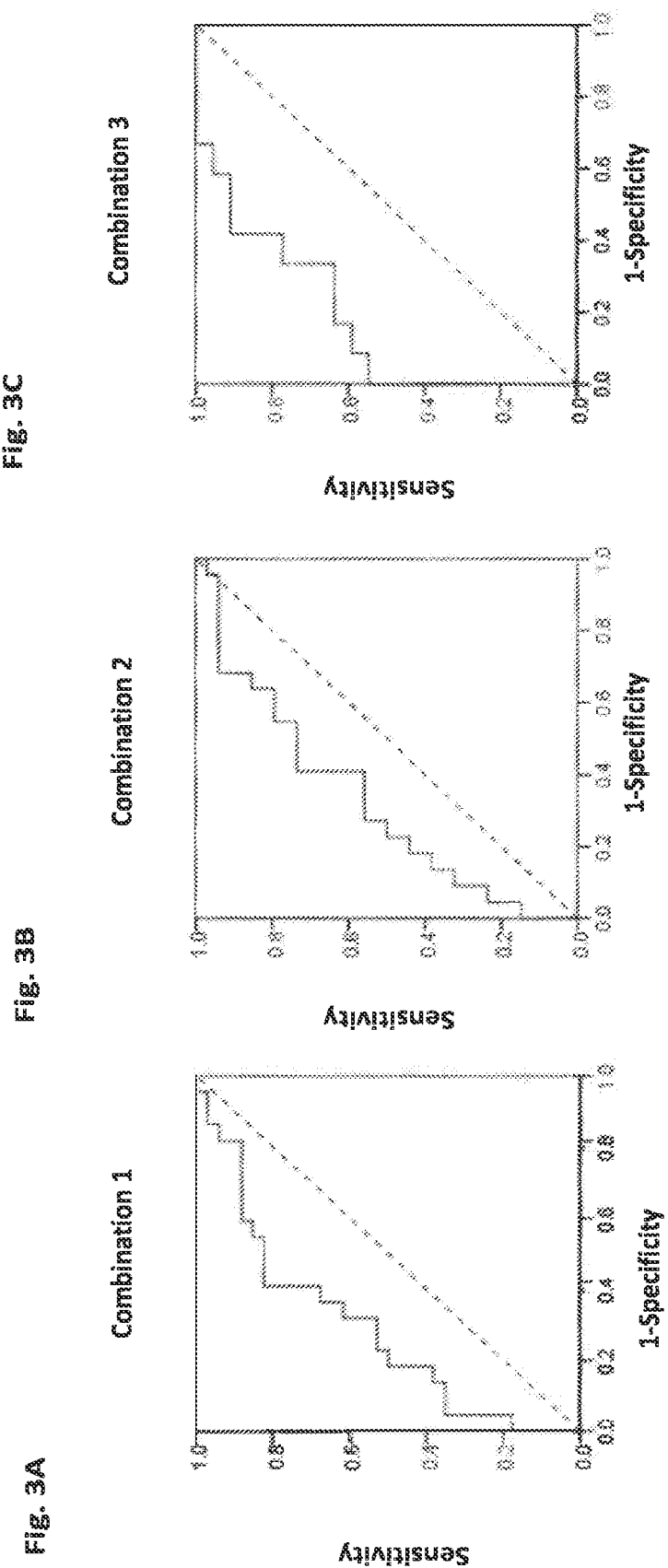

URINE MARKERS AND FORMULA FOR DIAGNOSING OVERACTIVE BLADDER DISORDER

CROSS-REFERENCE TO RELATED APPLICATIONS

This application is a national stage application of PCT/GB2019/050416, filed on Feb. 18, 2019, which claims priority to GB Application No. 1802653.4, filed on Feb. 19, 2018, which are hereby incorporated by reference in their entirety for all purposes.

FIELD OF INVENTION

The present invention relates to methods of diagnosing overactive bladder disorder (OAB), as well as methods of treatment and methods of monitoring disease progression. Kits for use in the diagnostic methods, computer systems and programs are also provided.

BACKGROUND TO THE INVENTION

As defined by the International Continence Society (ICS), overactive bladder (OAB) is a common condition encompassing several urinary symptoms, predominantly urinary urgency, dictating an abrupt and pressing need to urinate which is hard to defer, and may also include urge-associated urinary incontinence should involuntary leakage of urine occur. Further symptoms include urinary frequency rendering an individual to increase going to the bathroom during both day and night to often eight or more times within a 24 hour period, and nocturia leading to waking to go to the bathroom one or more times during the night.

OAB may be referred to as detrusor instability or irritable or unstable bladder. Two large studies show that approximately 1 in 5 adults suffer symptoms consistent with OAB, with 1 in 3 OAB sufferers experiencing urge incontinence. Extrapolation of results from a population-based survey infer an estimated 5.15 million sufferers of OAB in the United Kingdom in 2001. Within the study, 60% of those who suffered symptoms had consulted a practitioner, indicating a potentially larger population of OAB sufferers unaccounted for, with data on prevalence being underrepresented.

OAB is primarily diagnosed by taking patient medical history, assessing symptomology, physical examination and urinalysis. Diagnosis based on questioning includes determining the nature, onset, severity and duration of symptoms to evaluate whether these are consistent with OAB, impact on quality of life determined through an incontinence-specific quality of life questionnaire, medications taken, past and present health issues, and lifestyle factors e.g. diet, quantity and types of liquid consumed, details of which may be kept in a bladder diary. Risk factors also considered include ethnicity, age and BMI, e.g. white ethnicity have three times increased OAB risk. Physical examination is employed to exclude possible causes through assessing abdominal, gynaecological, genitourinary, rectal and neurological systems. Subsequent urinalysis identifies presence of nitrites, protein, glucose, blood and leucocytes in urine by a dipstick test to rule out possible UTI.

However, the current diagnostic techniques present a number of concerns. First, a questionnaire of urinary symptoms is not objective, subject to repeat variation and is highly influenced by factors such as diet and fluid intake. Second, the current gold standard, used by tertiary referral urology centres worldwide, requires the bladder's pressure to be monitored. The patient receives either a local or a general anaesthesia. A pressure transducer is placed into the bladder's lumen, via the urethra, and a second placed into the vagina or rectum. The clinician is seeking to make a positive diagnosis of "detrusor overactivity" based on the observation of involuntary contractions of the bladder's muscle (the detrusor) during filling of the bladder. Alas, around 50% of OAB patients do not exhibit this hallmark and 50% of asymptomatic individuals do; meaning that the technique cannot accurately diagnose OAB. The highly invasive and expensive (around £1,500 per assessment) nature of diagnosis prevents repeated monitoring, such as is required to tailor treatment. Furthermore, being hospital-based and requiring anaesthesia together mean this technique is not suitable for the frail elderly. As such, an accurate, non-invasive and inexpensive test is needed.

Potential biomarkers such as bladder wall thickness, urothelial adenosine triphosphate (ATP) release, nitric oxide, various cytokines, nerve growth factor (NGF) and prostaglandins have been considered for possible utility in diagnosing OAB. However, even where these putative biomarkers can be obtained non-invasively, they have as yet been unable to differentiate OAB from related bladder diseases with any reliability. Hence, there is still need for an accurate, non-invasive and inexpensive test.

SUMMARY OF THE INVENTION

The present inventors have identified combinations of biomarkers and confounders (age, gender, etc) that can be analysed using a novel algorithm to determine the probability that a subject has over active bladder disorder (OAB). A particular advantage of the present invention is that the biomarkers can be obtained non-invasively, which can improve the patient experience and significantly reduce costs associated with making a diagnosis.

Accordingly, in first aspect the present invention provides a method of diagnosing OAB, the method comprising:
  measuring the concentrations of adenosine triphosphate (ATP), acetylcholine (ACh), nitrite, monocyte chemoattractant protein 1 (MCP-1) and interleukin 5 (IL-5) in a sample obtained from a subject;
  normalising the concentrations to the concentration of creatinine (Cr) in the sample;
  range standardising the normalised concentrations and subject's age to the following values: Age to 120 years old; ATP/Cr to 0.000001 mole/mg×dl$^{-1}$; ACh/Cr to 0.1 mole/mg×dl$^{-1}$; Nitrite to 200 nM/mg×dl$^{-1}$; MCP-1/Cr to 100 pg×ml$^{-1}$/mg×dl$^{-1}$; IL-5/Cr 100 pg×ml$^{-1}$/mg×dl$^{-1}$;
  applying the normalised and range standardised concentrations to the following formula: Logit (p)=−1.738±1.404+4.985±2.914×subject's age+3315.959±5435.254×[ATP]/[Cr]+(−25204.194±20268.337)×[ACh]/[Cr]+26.799±32.967×[nitrite]/[Cr]+6.755±25.132 [MCP-1]/[Cr]+(−61.838±148.740) [IL-5]/[Cr] and calculating Logit;
  wherein a Logit value above a predetermined threshold indicates that the subject has OAB.

In a second aspect, the present invention provides a method of diagnosing OAB, the method comprising:
  measuring the concentrations of adenosine triphosphate (ATP), acetylcholine (ACh), nitric oxide (NO), nitrite, monocyte chemoattractant protein 1 (MCP-1) and interleukin 5 (IL-5) in a sample obtained from a subject;

normalising the concentrations to the concentration of creatinine (Cr) in the sample;

range standardising the normalised concentrations and subject's age to the following values: Age to 120 years old; ATP/Cr to 0.000001 mole/mg×dl$^{-1}$; ACh/Cr to 0.1 mole/mg×dl$^{-1}$; NO/Cr to 20,000 nM/mg×dl$^{-1}$; Nitrite to 200 nM/mg×dl$^{-1}$; MCP-1/Cr to 100 pg×ml$^{-1}$/mg×dl$^{-1}$; IL-5/Cr 100 pg×ml$^{-1}$/mg×dl$^{-1}$;

applying the normalised and range standardised concentrations to the following formula: Logit (p)=−6.396±6.732+1.664±1.363×gender+14.812±12.852×subject's age+8.625±31.214×volume+1362.442±3250.433×[ATP]/[Cr]+(−8323032±35168.325)×[ACh]/[Cr]+(−33.706±32.720)×[NO]/[Cr]+77.043±90.269×[nitrite]/[Cr]+(−4.895±48.360) [MCP-1]/[Cr]+(−2.759±202.207) [IL-5]/[Cr] and calculating Logit;

wherein a Logit value above a predetermined threshold indicates that the subject has OAB.

Confounders used in the diagnostic methods of the invention include subject characteristics such as age and/or gender. Gender may be coded for input to the algorithm, with 1 being female and 2 being male.

The biomarker concentrations are normalised to the concentration of urinary creatinine concentration, which is commonly used for biomarker standardisation. Creatinine is the breakdown product of creatinine phosphate metabolism of skeletal muscle tissue, which is filtered out of blood by kidneys and excreted in urine. Creatinine excretion is usually at a constant rate for an individual with a healthy renal function.

Preferably the confounders and normalised concentrations of the biomarkers (i.e., the independent variables) are range standardised on a 0 to 1 scale. In preferred embodiments of the invention each independent variable is range standardised to the highest possible number that can be measured for any one subject, i.e., age is range standardized to 120 years old; volume is range standardized to 1000 ml of urine; ATP/Cr is range standardized to 0.000001 mole/mg×dl$^{-1}$; ACh/Cr is range standardized to 0.1 mole/mg×dl$^{-1}$; NO/Cr is range standardized to 20000 nM/mg×dl$^{-1}$; Nitrite is range standardized to 200 nM/mg×dl$^{-1}$; MCP-1/Cr is range standardized to 100 pg×ml$^{-1}$/mg×dl$^{-1}$ and IL-5/Cr is range standardized to 100 pg×ml$^{-1}$/mg×dl$^{-1}$. This ensures that any measured value can be range standardised to the same values used in the algorithm of the present invention.

The diagnostic methods of both the first and second aspects of the invention have been shown to provide a high level of sensitivity and specificity for OAB (i.e. to distinguish OAB from other lower urinary tract symptoms), both reaching a satisfactory clinical accuracy of above 70%; far exceeding the accuracy of current gold-standard methods of diagnosis.

The outcome of the algorithm is a value of logit(p). For Logit(p)=y, the probability p of having a positive outcome (i.e. OAB) equals $1/1+e^{-logit(p)}$.

The determination of a high logit value is based on a threshold level, which is typically determined from a relevant population of individuals who are free from OAB. The relevant population can be defined based on, for example, diet, lifestyle, age, ethnic background or any other characteristic that can affect the normal levels of the markers. Once the threshold value is known, the measured logit value can be compared.

The significance of the difference between threshold and calculated logit values can be determined using standard statistical methods. If there is a substantial difference between the calculated logit and the threshold (i.e. a statistically significant difference), then the individual for whom the logit value has been calculated may be considered to have OAB. In embodiments of the invention, the logit value can be back-transformed to p (predicted probability of the subject having OAB) using the following formula: (predicted probability)=1/(1+e^logit(p)). p ranges from 0 (OAB uncertain, i.e. very unlikely) to 1 (OAB certain).

In preferred embodiments of the invention the sample is a urine sample. The sample can therefore be obtained non-invasively. This can significantly improve the patient experience compared to conventional diagnostic techniques relying on invasive urodynamics, especially where repeated assessments are required. The methods of the present invention can also significantly reduce costs associated with making a diagnosis of OAB by avoiding the need for the specialist equipment and skilled operators need for urodynamic assessments. By using a non-invasively obtained sample the diagnostic methods of the present invention can also enable diagnosis of OAB in patient groups for which current diagnostic methods are not suitable, such as the frail or elderly.

The subject is typically a mammal and is preferably a human. In embodiments of the invention the subject may be a paediatric or geriatric subject.

The biomarkers may be proteins, nucleic acids or biomolecules. Concentrations of the biomarkers can be measured using in vitro diagnostic platforms such as antibody-based platforms or RNA aptamer-based platforms or a combination thereof.

Diagnostic methods of the invention may further comprise administering a therapeutic agent to a subject diagnosed as having OAB. Accordingly, in a third aspect, the present invention provides a method of treating OAB, the method comprising diagnosing OAB in a patient using the methods described herein, and administering a therapeutic agent to the patient. As mentioned above, the diagnostic methods of the present invention are non-invasive (and therefore likely to be more acceptable to a patient and potentially cheaper than an alternative invasive procedure), which can allow OAB to be diagnosed an earlier stage. This may provide an improved outcome when treating the diagnosed OAB, as at later stages of the disease the symptoms appear to be only partially reversible.

Therapeutic agents for treating OAB are known in the art and include antimuscarinic drugs and a β3 adrenergic receptor agonists. An antimuscarinic drug may be selected from one or more of darifenacin, oxybutynin, tolterodine, solifenacin, trospium, flavoxate, propiverine or fesoterodine. A β3 adrenergic receptor agonist may be mirabegron.

In a further aspect the present invention provides a method of monitoring the progression of OAB, the method comprising measuring first and second logit values according to the diagnostic methods described herein, wherein the first and second logit values are obtained from first and second samples obtained from a subject having or suspected of having OAB. Monitoring disease progression also allows the effectiveness of OAB treatments to be monitored, for example, stage-specific responses to treatment may be monitored.

The first and second samples may be obtained at an interval of at least two weeks or at least four weeks, or more.

In this aspect of the invention the first logit value and/or second logit value may be compared to a projected logit value, established by testing the same subject at an earlier date and predicating the logit value that is likely to be observed if OAB progresses and/or if treatment of OAB is successful. The prediction may simply be an increase or decrease in the logit value, or it may be possible to quantify the likely change.

The present invention additionally provides a kit for use in the diagnostic methods described herein, the kit comprising binding molecules that specifically bind to one or more of adenosine triphosphate (ATP), acetylcholine (ACh), nitrite, monocyte chemoattractant protein 1 (MCP-1), interleukin 5 (IL-5) and creatinine (Cr). Preferably, the kit consists essentially of binding molecules that specifically bind to ATP, ACh, nitrite, MCP-1, IL-5 and Cr. In embodiments of the invention the kit may additionally comprise binding molecules that specifically bind to nitric oxide (NO).

The binding molecules may be antibodies or functional fragments thereof and may be labelled with a dye or a fluorescent molecule to allow binding of the molecule to the biomarker to be observed. The kit may comprise multiple parts, each configured to measure the concentration of one of the biomarkers. Alternatively, the kit may allow the concentrations of two or more of the biomarkers to be measured in combination. In this embodiment each binding molecule is preferably capable of producing a different detectable product.

The present invention additionally provides a computer system comprising processing means/a processor configured to execute instructions for:
receiving measured concentrations of adenosine triphosphate (ATP), acetylcholine (ACh), nitrite, monocyte chemoattractant protein 1 (MCP-1), interleukin 5 (IL-5) and creatinine (Cr);
normalising the concentrations of ATP, ACh, nitrite, MCP-1 and IL-5 to the concentration of Cr;
range standardising the normalised concentrations and subject's age to the following values: Age to 120 years old; ATP/Cr to 0.000001 mole/mg×dl$^{-1}$; ACh/Cr to 0.1 mole/mg×dl$^{-1}$; Nitrite to 200 nM/mg×dl$^{-1}$; MCP-1/Cr to 100 pg×ml$^{-1}$/mg×dl$^{-1}$; IL-5/Cr 100 pg×ml$^{-1}$/mg×dl$^{-1}$; and
calculating a Logit value by applying the normalised and range standardised concentrations to the following formula: Logit (p)=−1.738±1.404+4.985±2.914×subject's age+3315.959±5435.254×[ATP]/[Cr]+(−25204.194±20268.337)×[ACh]/[Cr]+26.799±32.967×[nitrite]/[Cr]+6.755±25.132 [MCP-1]/[Cr]+(−61.838±148.740) [IL-5]/[Cr] and calculating Logit.

In embodiments of the invention the computer system may comprise processing means/a processor configured to execute instructions for:
receiving measured concentrations of adenosine triphosphate (ATP), acetylcholine (ACh), nitric oxide (NO), nitrite, monocyte chemoattractant protein 1 (MCP-1), interleukin 5 (IL-5) and creatinine (Cr);
normalising the concentrations of ATP, ACh, NO, nitrite, MCP-1 and IL-5 to the concentration of Cr;
range standardising the normalised concentrations and subject's age to the following values: Age to 120 years old; ATP/Cr to 0.000001 mole/mg×dl$^{-1}$; ACh/Cr to 0.1 mole/mg×dl$^{-1}$; NO/Cr to 20,000 nM/mg×dl$^{-1}$; Nitrite to 200 nM/mg×dl$^{-1}$; MCP-1/Cr to 100 pg×ml$^{-1}$/mg×dl$^{-1}$; IL-5/Cr 100 pg×ml$^{-1}$/mg×dl$^{-1}$;
applying the normalised and range standardised concentrations to the following formula: Logit (p)=−6.396±6.732+1.664±1.363×gender+14.812±12.852×subject's age+8.625±31.214×volume+1362.442±3250.433×[ATP]/[Cr]+(−8323032±35168.325)×[ACh]/[Cr]+(−33.706±32.720)×[NO]/[Cr]+77.043±90.269×[nitrite]/[Cr]+(−4.895±48.360) [MCP-1]/[Cr]+(−2.759±202.207) [IL-5]/[Cr] and calculating Logit.

The present invention additionally provides a computer program comprising instructions which, when executed by a processor/processing means cause the processor/processing means to:
receive measured concentrations of adenosine triphosphate (ATP), acetylcholine (ACh), nitrite, monocyte chemoattractant protein 1 (MCP-1), interleukin 5 (IL-5) and creatinine (Cr);
normalise the concentrations of ATP, ACh, nitrite, MCP-1 and IL-5 to the concentration of Cr;
range standardise the normalised concentrations and subject's age to the following values: Age to 120 years old; ATP/Cr to 0.000001 mole/mg×dl$^{-1}$; ACh/Cr to 0.1 mole/mg×dl$^{-1}$; Nitrite to 200 nM/mg×dl$^{-1}$; MCP-1/Cr to 100 pg×ml$^{-1}$/mg×dl$^{-1}$; IL-5/Cr 100 pg×ml$^{-1}$/mg×dl$^{-1}$; and
calculate a Logit value by applying the normalised and range standardised concentrations to the following formula: −1.7381.404+4.985±2.914×subject's age+3315.959±5435.254×[ATP]/[Cr]+(−25204.194±20268.337)×[ACh]/[Cr]+26.799±32.967×[nitrite]/[Cr]+6.755±25.132 [MCP-1]/[Cr]+(−61.838±148.740) [IL-5]/[Cr] and calculating Logit.

In embodiments of the invention the computer program may comprise instructions which, when executed by a processor/processing means cause the processor/processing means to:
receive measured concentrations of adenosine triphosphate (ATP), acetylcholine (ACh), nitric oxide (NO), nitrite, monocyte chemoattractant protein 1 (MCP-1), interleukin 5 (IL-5) and creatinine (Cr);
normalise the concentrations of ATP, ACh, NO, nitrite, MCP-1 and IL-5 to the concentration of Cr;
range standardise the normalised concentrations and subject's age to the following values: Age to 120 years old; ATP/Cr to 0.000001 mole/mg×dl$^{-1}$; ACh/Cr to 0.1 mole/mg×dl$^{-1}$; NO/Cr to 20,000 nM/mg×dl$^{-1}$; Nitrite to 200 nM/mg×dl$^{-1}$; MCP-1/Cr to 100 pg×ml$^{-1}$/mg×dl$^{-1}$; IL-5/Cr 100 pg×ml$^{-1}$/mg×dl$^{-1}$;
applying the normalised and range standardised concentrations to the following formula: Logit (p)=−6.396±6.732+1.664±1.363×gender+14.812±12.852×subject's age+8.625±31.214×volume+1362.4423250.433×[ATP]/[Cr]+(−8323032±35168.325)×[ACh]/[Cr]+(−33.706±32.720)×[NO]/[Cr]+77.043±90.269×[nitrite]/[Cr]+(−4.895±48.360) [MCP-1]/[Cr]+(−2.759±202.207) [IL-5]/[Cr] and calculating Logit.

The present invention additionally provides a computer readable medium comprising the computer program described herein. Typically the machine readable medium is a non-transitory medium or a storage medium, especially a non-transitory storage medium.

The present invention can therefore be used to provide a point-of-care diagnostic test, which utilises a non-invasively obtained sample to quickly and easily diagnose and/or monitor OAB.

BRIEF DESCRIPTION OF THE DRAWINGS

The invention will now be described in detail, by way of example only, with reference to the figures.

FIG. 2 shows receiver line operating characteristic curves (ROCs) of OAB prediction models (individually). Diagonal line represents a non discriminatory test; stepped line shows the prediction model curve.

FIG. 2G shows an individual receiver line operating characteristic curve (ROC) of an OAB prediction model using nitrite (NO2-) concentration as the measured biomarker wherein the diagonal line represents a non-discriminatory test, and the stepped line shows the prediction model curve.

FIG. 2H shows an individual receiver line operating characteristic curve (ROC) of an OAB prediction model using nitrate (NO3-) concentration as the measured biomarker wherein the diagonal line represents a non-discriminatory test, and the stepped line shows the prediction model curve.

FIG. 3A shows the combined receiver line operating characteristic curve (ROC) of an OAB prediction model of variable combination 1 wherein the diagonal line represents a non-discriminatory test, and the stepped line shows the prediction model curve.

FIG. 3B shows the combined receiver line operating characteristic curve (ROC) of an OAB prediction model of variable combination 2 wherein the diagonal line represents a non-discriminatory test, and the stepped line shows the prediction model curve.

FIG. 3C shows the combined receiver line operating characteristic curve (ROC) of an OAB prediction model of variable combination 3 wherein the diagonal line represents a non-discriminatory test, and the stepped line shows the prediction model curve.

EXAMPLES

Methods

Urine Sample Collection, Transport and Processing

Figure 1:
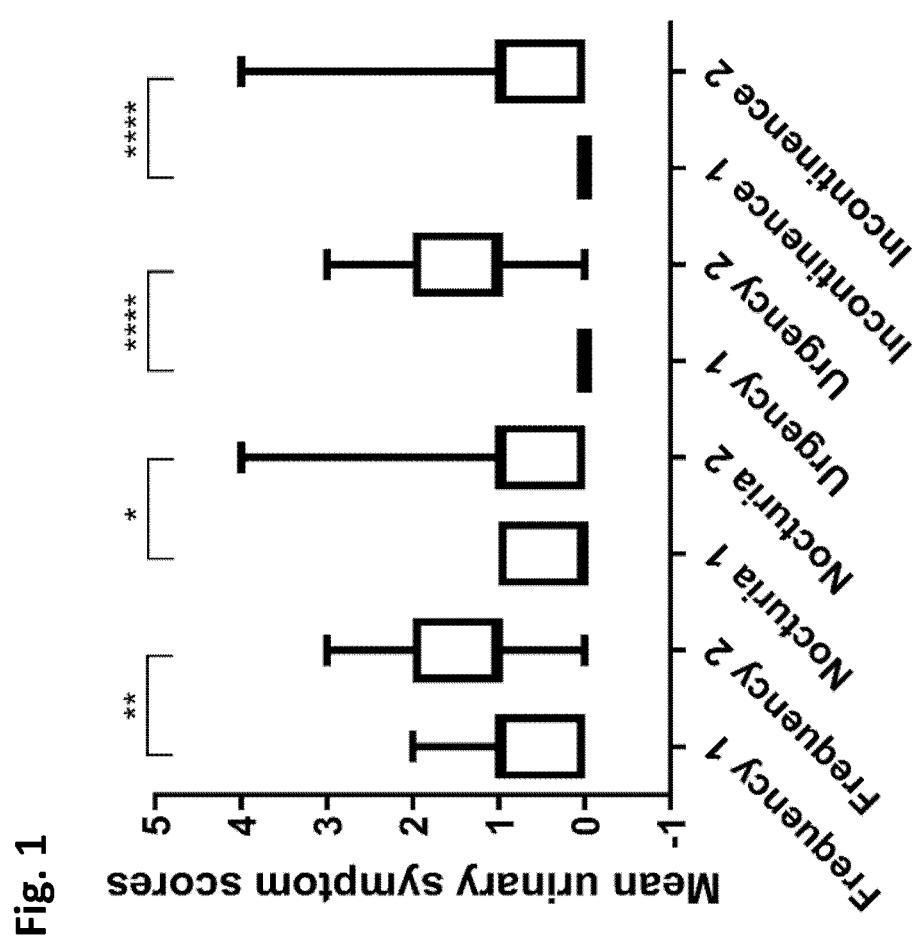
FIG. 1 shows the distribution of urinary symptoms amongst groups 1 and 2.*: p-value≤0.05; : significant, p-value≤0.01; **: significant, p-value≤0.0001.
Figure 2A:
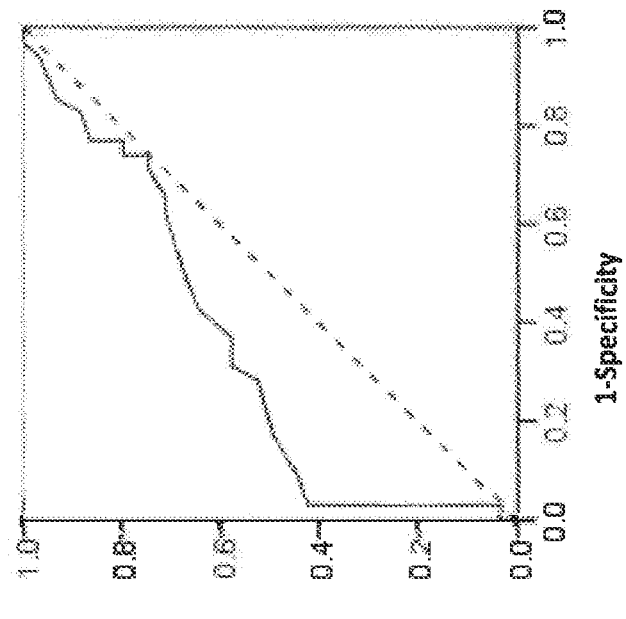
FIG. 2A shows an individual receiver line operating characteristic curve (ROC) of an OAB prediction model using gender as a confounder wherein the diagonal line represents a non-discriminatory test, and the stepped line shows the prediction model curve.
Figure 2B:
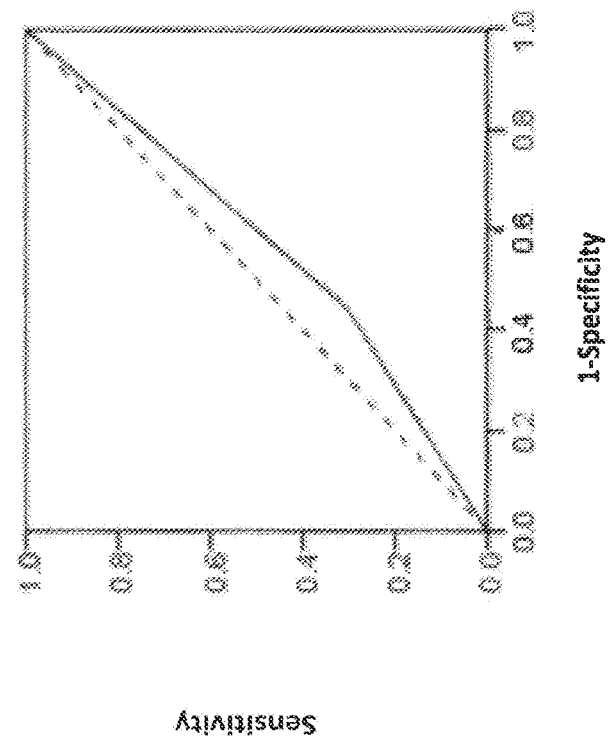
FIG. 2B shows an individual receiver line operating characteristic curve (ROC) of an OAB prediction model using age as a confounder wherein the diagonal line represents a non-discriminatory test, and the stepped line shows the prediction model curve.
Figure 2C:
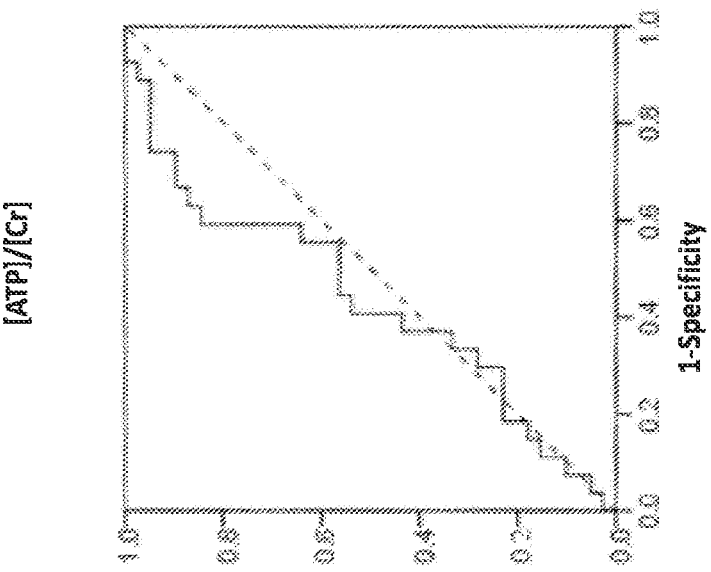
FIG. 2C shows an individual receiver line operating characteristic curve (ROC) of an OAB prediction model using urine volume as the measured biomarker wherein the diagonal line represents a non-discriminatory test, and the stepped line shows the prediction model curve.
Figure 2D:
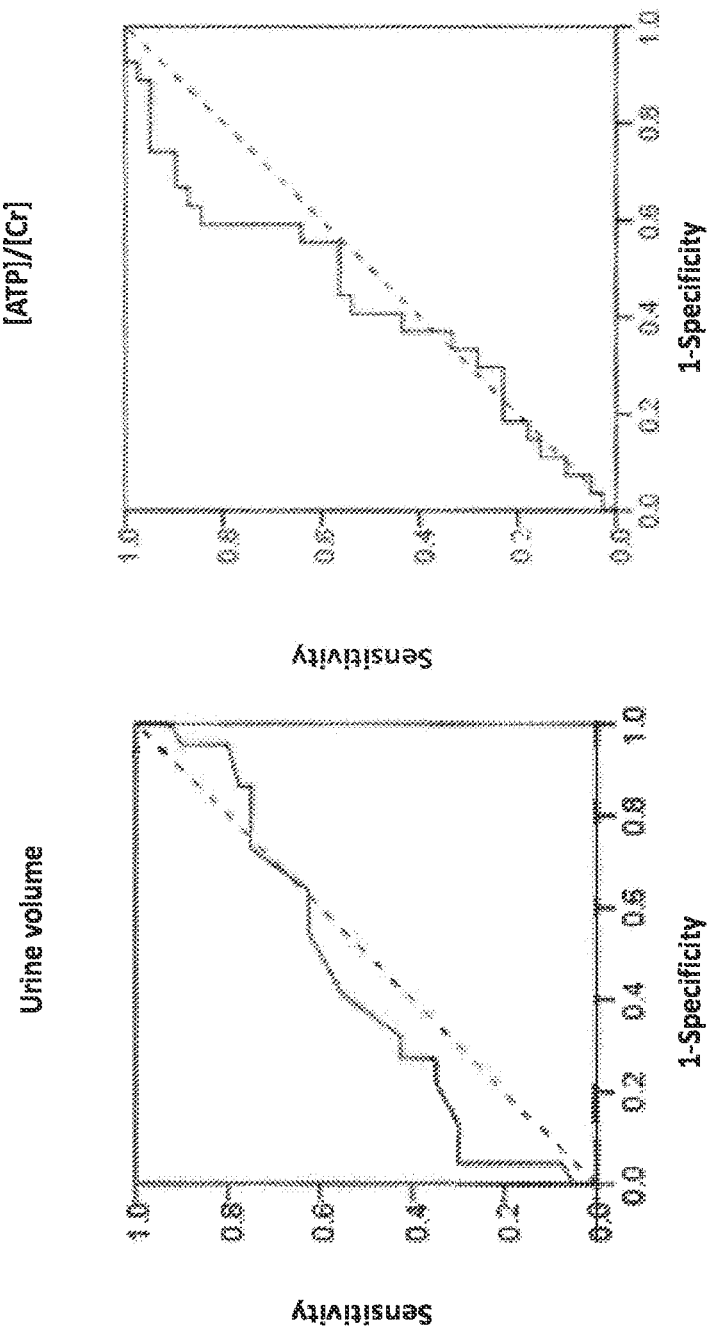
FIG. 2D shows an individual receiver line operating characteristic curve (ROC) of an OAB prediction model using adenosine triphosphate (ATP) concentration as the measured biomarker wherein the diagonal line represents a non-discriminatory test, and the stepped line shows the prediction model curve.
Figure 2F:
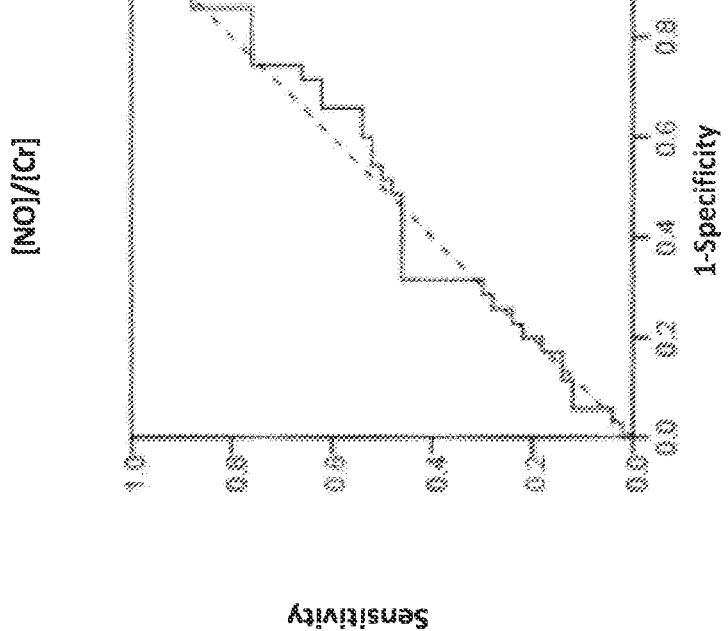
FIG. 2F shows an individual receiver line operating characteristic curve (ROC) of an OAB prediction model using nitric oxide (NO) concentration as the measured biomarker wherein the diagonal line represents a non-discriminatory test, and the stepped line shows the prediction model curve.
Figure 2E:
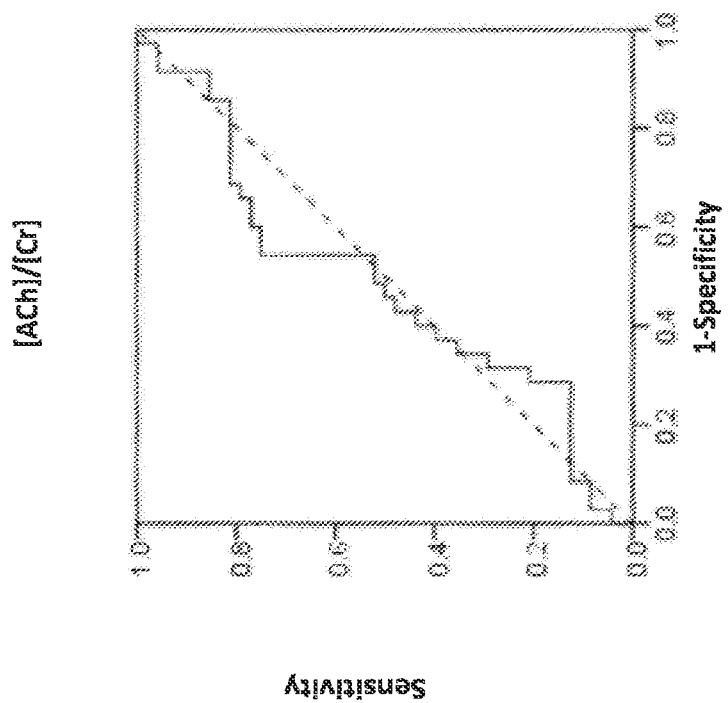
FIG. 2E shows an individual receiver line operating characteristic curve (ROC) of an OAB prediction model using acetylcholine (ACh) concentration as the measured biomarker wherein the diagonal line represents a non-discriminatory test, and the stepped line shows the prediction model curve.
Figures 2I, 2J:
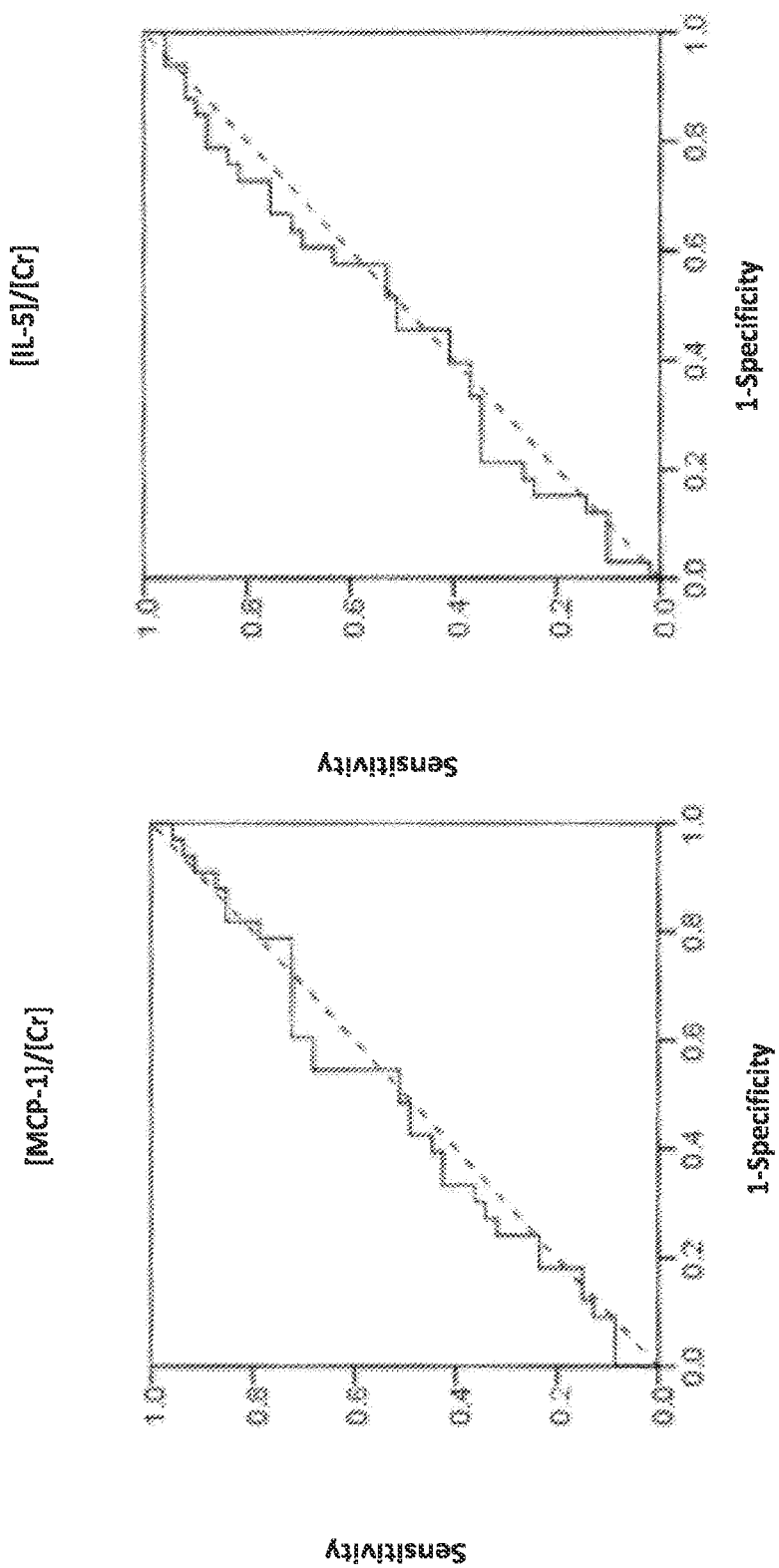
FIG. 2I shows an individual receiver line operating characteristic curve (ROC) of an OAB prediction model using monocyte chemoattractant protein 1 (MCP-1) concentration as the measured biomarker wherein the diagonal line represents a non-discriminatory test, and the stepped line shows the prediction model curve.
FIG. 2J shows an individual receiver line operating characteristic curve (ROC) of an OAB prediction model using interleukin 5 (IL-5) concentration as the measured biomarker wherein the diagonal line represents a non-discriminatory test, and the stepped line shows the prediction model curve.
Figure 4:
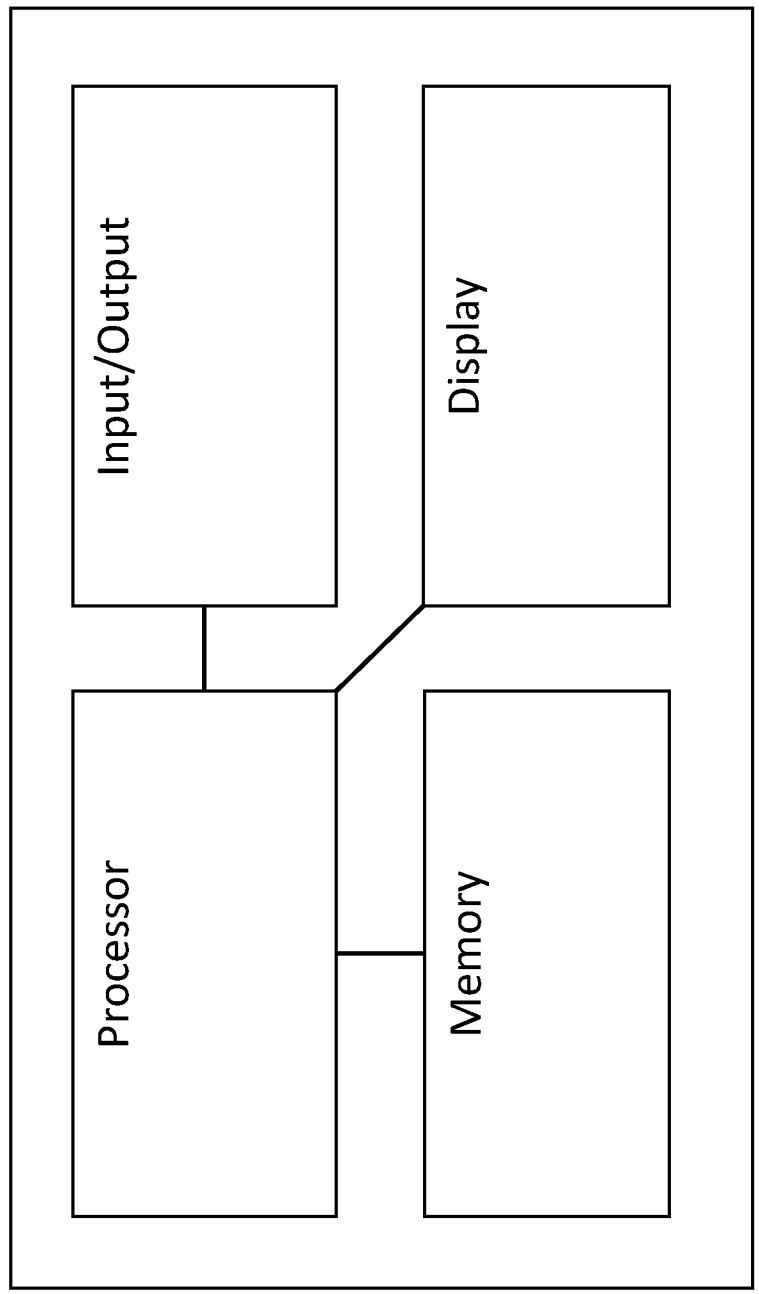
FIG. 4 shows a schematic illustration of a computer system configured to execute a computer program in line with the present invention. A computer [outer box] is shown. The computer is configured to execute a computer program to carry out the diagnostic method as described herein. The computer contains a processor, a memory, a display and an input/output for receiving data and/or outputting data.

This study and all its procedures were approved by the National Research Ethics Service (NRES) Committee South Central Berkshire, (REC reference: 13/SC/0501).

Study Participants/Recruitment

A total of 108 (35 male and 73 female, mean age: 55±18 years) volunteer participants were recruited from the staff and students of the University of Portsmouth (UoP) and from the residents/members of The Briars, Greensleeves Homes Trust, Isle of Wight; The National Federation of Women's Institutes; Portsmouth and Portsmouth Pensioners' Association. Volunteers were sought by direct recruitment with a verbal briefing prior to giving the Patient information Sheet (PIS); two copies of the consent form (participant's and researcher's copies) and ICIQ-OAB questionnaire. After consenting participants to the study, they were asked to complete ICIQ-OAB questionnaire and to provide a fresh urine sample (midstream, not first in the morning). Collected samples and data were made anonymous using an ID code system and were transferred to the UoP for analysis.

ICIQ-OAB Questionnaire

The ICIQ-OAB is a psychometrically robust instrument that quantifies the OAB symptoms of an individual. The questionnaire assesses the presence, absence and severity of urinary urgency, frequency, nocturia and incontinence symptoms individually and as a total urinary symptom score (Abrams et al. 2006). Each question is followed by a scale to assess associated bother. Appropriate consent for using the ICIQ-OAB questionnaire was sought from Dr Nikki Cotterill (on behalf of the ICIQ study group).

Inclusion/Exclusion Criteria

Inclusion Criteria:
  Age≥18
  Participant is willing and able to give informed consent for participation in the study
  Male or Female
Exclusion Criteria:
  Age<18
  Unable to consent
  The participant may not enter the study if ANY of the following apply: Diagnosed with neurologic disease (stroke, MS, Parkinson's disease, spinal cord injury);

have history of uterine, cervical, vaginal or urethral cancer; history of cyclophosphamide use (anti-tumour agent, its metabolite, acrolein, has been proven to cause haemorrhagic cystitis) or any type of chemical cystitis; history of benign or malignant bladder tumours; patients that have had Botulinium injections, neuromodulation or augmentation cystoplasty.

At the University of Portsmouth

Collected data were securely stored in an encrypted, physically-secured computer at the UoP. The Doctoral researcher was blinded to this information whilst running different tests on the collected samples. Pathology (including microscopic, chromogenic UTI medium and dipstick urinalysis tests) was immediately performed on a small proportion of each urine sample. Any positive test meant that a sample was considered 'unhealthy'.

Microscopic test: urine was mixed by inversion, 60 µl of urine was dispensed (in duplicate) into a flat-bottomed microtitrate tray, left to settle for a minimum of 5 minutes and then was examined under an inverted light microscope (×20 objective). Cells were counted/estimated per representative field and results were reported according to Table 1.

TABLE 1

Guidelines for reporting urine microscopy results (adopted from Hampshire Hospitals NHS foundation Trust, Microbiology department).

|  | Number per field | Reported as |
| --- | --- | --- |
| White blood cells (WBC) or Red blood cells (RBC) | 0 | Not seen |
|  | <5 | +/- |
|  | 5-15 | + |
|  | 15-50 | ++ |
|  | >50 | +++ |
| Epithelial (urothelial) cells | <3 | +/- |
|  | 3-5 | + |
|  | 5-10 | ++ |
|  | >10 | +++ |
| Organisms | Scanty | + |
|  | Moderate | ++ |
|  | Profuse | +++ |
| Casts (e.g. hyaline, granular, cellular, and waxy). Casts should be double checked by another appropriate person if unsure. | 0-5 |  |

Chromogenic medium UTI test: urine samples were cultured on to the Brilliance™ UTI chromogenic media (PO0794A, Thermo Scientific, UK) in order to detect any bacterial infection. Plates were incubated for 16-24 hours at 37° C. and results were reported based on the following diagnostic colony colour codes: Pink/Red: *Escherichia coli*; Turquoise/Blue-Green: Enterococci; Dark Blue/Purple: coliforms; Brown halo: *Proteus, Morganella* and *Providencia*; Brown/Green translucent: *Pseudomonas*; Non-pigmented White: *Staphylococci/Streptococci*; Pink: *Staphylococcus Saprophyticus*.

Dipstick test: Urine dipsticks were used to detect any obvious urinary tract abnormalities specifically urinary tract infection (UTI). The dipstick reagent strip contained test pads for the following analytes: leukocytes (indicative of pyuria associated with UTI); nitrite (indicative of urinary tract infection); urobilinogen (abnormal levels: indicative of liver problems); protein (abnormal levels/proteinuria: indicative of renal disease); pH (it can range between 4.5 and 8, but it is usually acidic (5.5-6.5), alkaline urine may be associated with UTI and/or calculi); occult blood (haematuria, common causes: UTI, kidney infection, kidney stones, etc.); Specific Gravity (gives an insight into the patient's hydration status); Ascorbic Acid (vitamin C, high levels has been associated with false-negative reagent strip reactions for glucose and occult blood); Ketone (product of body fat metabolism, it is usually associated with uncontrolled diabetes, but can be also detected during pregnancy, with carbohydrate-free diets and starvation); Bilirubin (indicative of liver disease or obstruction of the bile ducts) and Glucose (most commonly associated with diabetes mellitus). Results were obtained by direct comparison of the colour blocks printed on dipstick bottle label.

The remainder of the urine sample was centrifuged (at 4000 rpm, for 10 minutes, at 4° C.) and separated into its relevant constituents, cell pellet and supernatant, and were stored at −80° C. freezer. At a later date, the concentrations of the considered biomarkers were determined by subjecting supernatant samples to the following assays:

Biomarker Assays

The urinary concentrations of ATP, ACh, Nitrite, total NO, MCP-1 and IL-5 were measured in 99 of the collected samples (results not shown). Firstly, participants who were diagnosed as 'unhealthy' by urinalysis (due to yeast/bacterial infection or haematuria) were excluded and the measured biomarkers' concentrations were correlated with participants' individual and total urinary symptoms, bothersome and urinary symptoms plus associated bothersome scores. All data points represent an average of duplicate determinations which were normalized using creatinine concentrations (i.e. [biomarker]/[Creatinine]). Amongst the collected samples, 28 participants were taking one or more medicines, that are associated with urinary symptoms (MAUS), including oral oestrogens, alpha blockers, antidepressants, sedative-hypnotic, angiotensin-converting-enzyme inhibitor (ACE) inhibitors, angiotensin II receptor blockers (ARBs), beta blockers (BB), calcium channel blockers (CCB), diuretics, antihistamines and non-steroidal anti-inflammatory drugs (NSAIDs). Therefore, in order to evaluate any imposed effects of MAUS on the observed correlation results, these samples were excluded (in addition to 'unhealthy' data) and biomarkers' data were re-correlated with participants' individual and total urinary symptoms, bothersome and urinary symptoms plus associated bothersome scores. The distributions of the biomarkers' concentrations were also studied between participants, sub-grouped based on their medication status (i.e. taking no medication, taking MAUS, taking other medicines). Furthermore, the concentrations of biomarkers ('unhealthy' data excluded) were correlated with participants' age and total collected urine volumes, and their distribution levels were further studied with respect to participants' urine appearances (i.e. pale, normal, dark and red/orange and/or cloudy) and sleeping disorders. Finally, biomarkers' concentrations (all samples included) were shown on additional correlation graphs which were colour coded based on participants' health status determined based on pathology tests' results, i.e. healthy (N=69, i.e. no UTI or any other kidney/bladder complications); intermediate (N=11, i.e. suspicious of having UTI or any other kidney/bladder complications) and unhealthy (N=10, diagnosed as having UTI or any other kidney/bladder complications). The distribution levels of the biomarkers were also studied between these health-based subgroups.

Moreover, the relationship between the urinary levels of ATP and ACh, ATP and NO, and ACh and NO were investigated.

Creatinine Assay

Urinary creatinine levels were used as an index of standardisation for all the biomarker assays, i.e. all the urinary biomarker values were normalized to their corresponding urinary creatinine (Cr) levels ([biomarker]/[Cr]). Creatinine was measured using the Cayman Creatinine (urinary) Colourimetric Assay Kit (CAY500701, Cambridge Bioscience, UK). The assay relies on the change in colour intensity produced when the creatinine is first treated with alkaline picrate to produce a yellow/orange colour, and subsequently with an acidic solution to destroy the produced colour. The difference in the intensity of the colour before and after acidification is directly proportional to the creatinine concentration (Cayman Chemical 2014). For this assay, all the urine samples were diluted 1:10 with deionized water and were aliquoted, in duplicates, in to 96 well plates (Ser. No. 10/010,571, Fisher Scientific, UK). The absorbance was read at 492 nm (POLARstar Optima microplate reader, BMG LABTECH, UK) and creatinine was calculated using the following formula:

$$\text{Creatinine}\left(\frac{mg}{dl}\right) = \left[\frac{\text{sample absorbance} - (y \text{ intercept})}{\text{slope}}\right] \times \text{sample dilution}$$

ATP Assay

The concentration of ATP in each urine sample was measured using the ENLITEN® luciferin-luciferase (LL) bioluminescence assay (FF2000, Promega, UK). Luciferin is a light-emitting compound found in fireflies. In this assay, Luciferase; an oxidative enzyme; consumes ATP in order to catalyse the D enantiomer of Luciferin (D-Luciferin). Light is produced as by-product of this consumption, which can be directly measured in a luminometer and is proportional to ATP concentration.

Standard curves of $10^{-16}$-$10^{-7}$M were prepared from ATP powder (Sigma-Aldrich, A2383, UK) in deionized water. 40 µL of each standard and urine samples, in duplicates, were aliquoted in to 96 half-well plates (781610, BRANDplates®, pureGrade™, UK). The luminescence was measured (POLARstar Optima microplate reader, BMG LABTECH, UK) before the addition of LL mixture. Then, 40 µL of the reconstituted LL mixture was added to each well and luminescence was measured again. The relationship between the concentration of ATP in standards and luminescence values was determined by fitting the best (with highest r2 value) trendline for the produced data (Excel, Microsoft). The subsequent standard curve was used to interpolate the ATP concentrations of the unknown urine samples from their respective luminescence values. The ATP concentrations were normalised to their urinary creatinine values (ATP/Cr).

ACh Assay

Urinary ACh concentrations were measured using the Amplex® Red Acetylcholine/Acetylcholinesterase assay (Invitrogen™ Molecular Probes™, A12217, UK). The Acetylcholinesterase provided in this kit, converts the urinary ACh to Choline. Choline is then oxidized by Choline Oxidase to betaine and Hydrogen peroxide ($H_2O_2$). Amplex Red reagent (10-acetyl-3,7-dihydroxyphenoxazine) is a sensitive fluorogenic probe for $H_2O_2$, and in the presence of horseradish peroxidase, it generates a highly fluorescent product called Resorufin. Therefore, the amount of generated fluorescent product Resorufin is proportional to the urinary ACh concentration. In this study, standards (10-16-10-7M) and urine samples (in duplicates) were aliquoted in to 96 half-well plates (781610, BRANDplates®, pureGrade™, UK). The fluorescence was measured (POLARstar Optima microplate reader, BMG LABTECH, UK) using excitation at 540 nm and fluorescence detection at 590 nm. The ACh concentrations were normalised to urinary creatinine (ACh/Cr).

NO Assay

Nitric Oxide (NO) has a short half-life and is converted rapidly to its oxidation products Nitrite ($NO_2^-$) and Nitrate ($NO_3^-$). Urinary levels of NO, $NO_2^-$ and $NO_3^-$ were measured using the Sievers Nitric Oxide Analyser (NOA™ 280i, Analytix, UK).

Nitrite ($NO_2^-$)

$NO_2^-$ is produced when NO reacts with dissolved oxygen ($O_2$). To measure $NO_2^-$ the reducing agent iodide in glacial acetic acid is used to convert nitrite to nitric oxide (at ambient temperature):

$$I^- + NO_2^- + 2H^+ \rightarrow NO + \tfrac{1}{2}I_2 + H_2O$$

Under these conditions only the Nitrite and S-Nitrosothiol (if present) would be reduced to NO for measurement.

Nitrate ($NO_3^-$)

$NO_3^-$ the major oxidation product of NO in most physiological fluids and is produced when NO reacts with oxy-haemoglobin or superoxide anion. To measure nitrate, Vanadium (III) Chloride in 1N hydrochloric acid is used to convert nitrate to nitric oxide (at 95° C.):

$$2NO_3^- + 3V^{3+} + 2H_2O \rightarrow 2NO + 3VO_2^+ + 4H^+$$

Under these conditions not only would the Nitrite and S-Nitrosothiol be reduced to NO but also the Nitrate. Therefore the 'total NO' is the same as the 'Nitrate'. Therefore, Nitrate is calculated by deducting the 'Nitrite' value from the 'total NO' value. The NO, $NO_2^-$ and $NO_3^-$ concentrations were normalised to their respective urinary creatinine values (NO/Cr, $NO_2^-$/Cr and $NO_3^-$/Cr).

MCP-1 Assay

The concentration of urinary MCP-1 was quantified using BD OptEIA™ human MCP-1 enzyme-linked immunosorbent assay (ELISA) (559017, BD biosciences, UK). This assay is a solid phase sandwich ELISA that uses a monoclonal antibody specific for MCP-1 coated on 96-well plates. All of the urine samples and standards (100 µL) were added to the plates in duplicate and incubated at room temperature for 2 hours. After washing, the plates were incubated with horseradish peroxide (HRP)-conjugated anti-mouse secondary antibody for one hour. After sequential washing, the tetramethylbenzidine (TMB) substrate solution (30 minutes incubation in the dark) was used to detect HRP activity by yielding a blue colour that changed to yellow upon the addition of stop solution (1M phosphoric acid). The absorbance was read at 492 nm (POLARstar Optima microplate reader, BMG LABTECH, UK). The MCP-1 concentrations were normalised to urinary creatinine (MCP-1/Cr).

IL-5 Assay

The levels of urinary IL-5 were measured using the Quantikine® human IL-5 ELISA Kit (R&D Systems®, D5000B, UK) and the OptEIA™ Human IL-5 ELISA Set (555202, BD biosciences, UK). In summary, 100 µL of the urine samples and standards were added to the plates coated with a monoclonal antibody specific for human IL-5. After the incubation period and subsequent washes, an enzyme (HRP)-linked secondary antibody was added to the wells and incubated for 1-2 hours. Following a wash to remove any unbound antibody-enzyme reagent, a substrate solution was added to the wells. A blue colour developed which was proportional to the amount of IL-5 bound in the first step and the colour development was stopped and changed to yellow by the addition of the stop solution. The intensity of the colour was measured at 429 nm by a microplate reader (POLARstar Optima, BMG LABTECH, UK). The IL-5 concentrations were normalised to urinary creatinine (IL-5/Cr).

Statistical Analysis

Normality and, where appropriate, homogeneity of variance tests were performed on all the generated data to assess their distribution and based on this information the most suitable statistic tests were performed. Pearson product-moment correlation coefficient (parametric data) or Spearman's rank correlation coefficient (for non-parametric data) were used for correlation analysis; unpaired student's t-test (parametric data) or Mann-Whitney U-tests (non-parametric data) were used for statistical analysis between groups and ordinary (parametric data) or Kruskal-Wallis (non-parametric) one way ANOVA tests were used for multiple comparisons.

Cluster Analysis

Cluster analysis was performed using IBM SPSS statistics 22.0 on the data obtained from ICIQ-OAB questionnaire. Cluster analysis was run on different aspects of data obtained from the ICIQ-OAB questionnaire in order to identify the best combination of urinary characteristic scores that could be used to classify OAB patients. This included classification based on data acquired from urinary symptom scores, urinary symptom bothersome scores or urinary symptom scores plus bothersome scores from all (N=108) and all minus 'unhealthy' (i.e. N=(108−10) 98) participants. The distribution of responses to each question (symptom/bothersome measure) was range standardized on a 0 to 1 scale.

SPSS has three different approaches that can be used for cluster analysis: hierarchical cluster analysis, k-means cluster and two-step cluster analysis. Hierarchical cluster analysis attempts to reveal relatively homogenous clusters of cases (e.g. patients) or variables (e.g. measured characteristics of patients) using an algorithm to join cases/variables into larger clusters based on a measure of similarity or distance, and produces a hierarchical tree. Hierarchical clustering necessitates a distance or similarity matrix between all pairs of cases/variables, which makes it unsuitable for large set of data. In contrast, the algorithm used in k-means cluster analysis classifies cases/variables based on their distance to the cluster mean. 'k' is the number of clusters needed by the researcher that must be defined in advance. Both of these aforementioned methods identify clusters based on cases or variables; whereas, the two-way cluster analysis is used in circumstances where both cases and variables will simultaneously contribute to the detection of meaningful clusters. Two-way cluster analysis can be applied to both continuous and categorical data (individually and in combination). Its algorithm is based on a distance measure that gives the best results if all variables are independent, and continuous variables have a normal distribution, and categorical variables have a multinomial distribution (i.e. a distribution that displays the likelihood of the possible outcomes of an experiment with repeated trials in which each trial can result in a specified number of outcomes that is greater than two, such as results of tossing a dice which is in contrast to tossing a coin that has binominal distribution). However, in real practice it is rare to have continuous variables with a normal distribution; nevertheless the algorithm performs reasonably well when the assumptions are not met (Norusis 2008). The continuous variables used in this study were not any exceptional from real practice and did not display normal distributions when they were tested by D'Agostino and Pearson omnibus normality test (GraphPad Prism 6 software). Cluster analysis is mainly a descriptive addition and does not involve the calculation of observed significance levels, hence, it is faultlessly acceptable to cluster this data using two-way analysis method for the best performance (Norusis 2008).

Mann-Whitney U-Test

Mann-Whitney U-tests (non-parametric data) were used for statistical analysis between groups (GraphPad Prism 6 software).

Correlation Analysis

Spearman's rank correlation coefficient (GraphPad Prism 6 software) was used for correlation analysis between the dependent variable (OAB symptomatic) and the independent variables (participants' age, gender, total collected urine volume and urinary concentrations of ATP, ACh, NO, Nitrite, Nitrate, MCP-1 and IL-5).

Binary Logistic Regression

The ability of the identified biomarkers, individually or in combination (in different combination settings and with confounders (age, gender, collected urine volume)), in predicting the probability of someone being OAB symptomatic was studied using binary logistic regression test (IBM SPSS statistics 22.0). Outcome was coded as 0 (OAB asymptomatic) and 1 (OAB symptomatic), and gender was coded as 1 (female) and 2 (male) before being entered into SPSS software. All the independent variables were range standardized on a 0 to 1 scale. In this case, instead of standardizing each variable to its highest available measured value, each variable was range standardized to the highest possible number that could be measured for any one human (although for some of the urinary biomarkers the considered standardized numbers were so high that are almost impossible to be seen in any individual's urine; these high numbers were chosen just to be on the safe side and to enable the logit formula to be used for anyone) i.e. age was range standardized to 120 years old; volume was range standardized to 1000 ml of urine; ATP/Cr was range standardized to 0.000001 mole/mg×dl$^{-1}$; ACh/Cr was range standardized to 0.1 mole/mg×dl$^{-1}$; NO/Cr was range standardized to 20000 nM/mg×dl$^{-1}$; Nitrite was range standardized to 200 nM/mg×dl$^{-1}$; Nitrate was range standardized to 20000 nM/mg×dl$^{-1}$; MCP-1/Cr was range standardized to 100 pg×ml$^{-1}$/mg×dl$^{-1}$ and IL-5/Cr was range standardized to 100 pg×ml$^{-1}$/mg×dl$^{-1}$. This way, any measured value in the future could be range standardized to the same values used in this study and consequently could be placed in the generated logit formulae to estimate the probability of the presence of OAB. Before performing the logistic regression test, the strength of the potential relationship (i.e. strength of each predictor in the prediction model) between the dependent variable (outcome/asymptomatic or symptomatic) and the independent variables (participants' age, gender, total collected urine volume, measured urinary biomarkers) was assessed using correlation test (IBM SPSS statistics 22.0). Furthermore, the correlation test was also used to assess the multicollinearity between independent variables. The issue of multicollinearity occurs when there is an inter-correlation between two independent variables (both variables are explaining the same thing), this would create some redundancies and the independent variables may suppress each other's effect. Any two independent variables with an r-value above 0.80 are considered inter-correlated; therefore, either one of them should be eliminated or they need to be combined with each other before being placed in the logistic regression model.

Receiver Operating Characteristic (ROC) Analysis

ROC curve analysis (IBM SPSS statistics 22.0) was used in order to evaluate the sensitivity and specificity of the generated OAB prediction models using predicted probability (PRE) values generated by logistic regression analyses.

In a ROC curve the true positive rate (y-axis, sensitivity) is plotted against the false positive rate (x-axis, cases without the disease classified as positive, 1-specificity). The ability of the generated models to discriminate between positive (symptomatic) and negative (asymptomatic) cases are quantified via the area under the ROC curve (AUC). The maximum value for the AUC is 1.0 (100% sensitivity, 100% specificity); therefore, the closer the ROC curve is to the upper left corner, the higher the overall accuracy of the diagnostic test. A straight diagonal line extending from the lower left corner to the upper right corner presented in ROC curves (a.k.a. chance line) has an AUC value of 0.5 which reflects the performance of a diagnostic test that is no better than chance level, i.e. diagnostic test has no discriminative value. There are several different AUC scales available for classifying the accuracy of a diagnostic test, but, generally the following scales are used to interpret the performance of a diagnostic test:

AUC value of 0.9-1=excellent discriminatory power
AUC value of 0.8-0.9=good discriminatory power
AUC value of 0.7-0.8=fair discriminatory power
AUC value of 0.6-0.7=poor discriminatory power
AUC value of 0.5-0.6=no discriminatory power Results
Cluster Analysis Two-step cluster analysis was performed in order to identify natural groupings (clusters) amongst 108 participants based on their urinary data obtained via ICIQ-OAB questionnaire. Participants were clustered based on different aspects of their urinary data in order to identify the best OAB classifying method using information provided by the ICIQ-OAB questionnaire. These include cluster analysis performed based on urinary symptom scores only, urinary symptom bothersome scores only or urinary symptom scores plus bothersome scores, in all participants (AP, N=108) and in all but those designated as 'unhealthy' (AP-U, n=98, i.e. diagnosed as having yeast/bacterial infection or haematuria). Participants with missing answers for any of the symptom or bothersome questions were excluded from the cluster analyses.

Two natural clusters were identified amongst participants in all the cluster analyses run based on different aspects of the questionnaire data (Table 2). Highest numbers of participants were involved in the analyses (for both AP and AP-U groups) when urinary symptom scores (i.e. frequency score, nocturia score, urgency score and incontinence score) were used to cluster participants (Table 2); in other words, lower numbers of participants left urinary symptom related questions blank in the questionnaire compared to symptom bothersome questions. Therefore clusters formed based on urinary symptoms have higher statistical power to determine natural groupings compared to the clusters formed using other aspects of the questionnaire data (i.e. symptom bothersome score/symptom scores plus symptom bothersome scores). The quality of the identified clusters based on symptom scores were 'highly fair' for both groups (Table 2). Frequency was the most important cluster predictor component for the AP group, whereas urgency was the main cluster predictor component for AP-U group (Table 2). This clearly indicates the effect of the involvement of those with urinary tract infection (as majority (9 out of 10) of the participants in 'unhealthy group had UTI) in cluster analysis, as these patients mainly suffer from urinary frequency rather than urgency (Table 2). In contrast, urgency is the key identifier symptom in overactive bladder patients and should be the main predictor for clustering participants into OAB symptomatic or asymptomatic groups. Consequently, in order to assess the prediction ability, sensitivity and specificity of the identified urinary biomarkers in diagnosing patients with OAB, data obtained from the cluster analysis of AP-U group were subjected to further statistical analyses. Amongst 95 participants, 37.9% were assigned to group 1 and 62.1% of the participants were assigned into group 2 (Table 2). FIG. 1 shows the distribution of urinary symptoms amongst the two identified groups. Half (box plot in FIG. 1) of the participants in group 1 were visiting bathroom every three hours or more (score 0-1); were not waking up to void or had to wake up to void only once during the night (score 0-1) and were not suffering from urgency (score 0) or incontinence (score 0). In contrast, half (box plot in FIG. 1) of the participants in group 2 were visiting bathroom every two hours (score 1-2); were not waking up to void or had to wake up to void once during the night (score 0-1) (although some were waking up four times or more); were experiencing feeling of urgency every so often (score 1-2) and were having involuntary leakage of urine about once a week (score 0-1). In general, group 1 had significantly lower urinary symptom scores compared to group 2 and therefore group 1 was designated as 'healthy/OAB asymptomatic' group whereas group 2 was designated as 'OAB/symptomatic' group for further analyses.

TABLE 2

Identified clusters via two-step cluster analysis

| | Cluster analysis component(s) | n | Number of identified clusters | Cluster quality | Cluster size | Cluster predictor importance rank |
|---|---|---|---|---|---|---|
| All samples | Urinary symptom scores | 105 | 2 | Highly fair | Group 1 (64.8%), Group 2 (35.2%) | F >> N > U > I |
| | Urinary symptom bothersome scores | 88 | 2 | Good | Group 1 (65.9%), Group 2 (34.1%) | U >> I >> F > N |
| | Urinary symptom scores + bothersome scores | 88 | 2 | Good | Group 1 (67.0%), Group 2 (33.0%) | U >> I >> F > N |
| All samples minus UTI samples | Urinary symptom scores | 95 | 2 | Highly fair | Group 1 (37.9%), Group 2 (62.1%) | U >> I > F > N |

TABLE 2-continued

| Identified clusters via two-step cluster analysis | | | | | |
|---|---|---|---|---|---|
| Cluster analysis component(s) | n | Number of identified clusters | Cluster quality | Cluster size | Cluster predictor importance rank |
| Urinary symptom bothersome scores | 81 | 2 | Good | Group 1 (63.0%) Group 2 (37.0%) | U > I > F > N |
| Urinary symptom scores + bothersome scores | 81 | 2 | Good | Group 1 (72.8%) Group 2 (27.2%) | I >> U >> F > N | n: number of participants involved in the analysis; F: Frequency; N: Nocturia; U: Urgency; I: incontinence.

Correlation Test

The correlation between the dependent variable (outcome i.e. OAB symptomatic) and the independent/predictor variables (i.e. participants' age, gender, total collected urine volume and urinary concentrations of ATP, ACh, NO, Nitrite, Nitrate, MCP-1 and IL-5) was studied using Spearman's rank correlation coefficient (non-parametric data). Results are summarized in Table 3. Amongst the 10 predictor variables, Age, ATP, ACh, Nitrite, MCP-1 and IL-5 showed positive correlations with the dependent variable (outcome), though the correlation was only statistically significant with age (p=0.008), which suggests that age may be a strong predictor of the outcome when it is subjected to logistic regression test. When the correlation between the independent variables were assessed, a high inter-correlation (r-value=1) was observed between NO and Nitrate (Table 3), which indicates that one of them needs to be eliminated before being subjected to logistic regression analysis in biomarker combination model setups.

used as a prediction model individually, none could increase the prediction ability above the null hypothesis (the probability of assigning someone to symptomatic group (i.e. the probability of correct prediction) in the absence of any predictor variables) percentage range. In order to assess whether a combination of these independent variables will improve the prediction power, three different combinational models were created and subjected to binary logistic test. Combination 1 was created based on those independent variables that had shown positive correlations with symptomatic outcome (i.e. age, ATP/Cr, ACh/Cr, Nitrite/Cr, MCP-1/Cr and IL-5/Cr), combination 2 included all the urinary biomarkers (without confounders [gender, age and urine volume]) and combination 3 comprised all the independent (urinary biomarkers and confounders) variables. Amongst the three models, combination 1 increased the OAB prediction ability to the highest (12.5%) from null hypothesis, but combination 3 had superior overall predic-

TABLE 3

The correlation between the dependent variable (OAB symptomatic) and the independent variables (participants' age, gender, total collected urine volume and urinary concentrations of ATP, ACh, NO, Nitrite, MCP-1 and IL-5).

| | | Clusters | Gender | Age | Volume | ATP/Cr | ACh/Cr | NO/Cr | Nitrite/Cr | Nitrate/Cr | MCP-1/Cr | IL-5/_Cr |
|---|---|---|---|---|---|---|---|---|---|---|---|---|
| Clusters | r-value | 1.000 | −0.141 | 0.274 | −0.090 | 0.121 | 0.031 | −0.011 | 0.116 | −0.030 | 0.043 | 0.057 |
| | p-value | | 0.173 | 0.008 | 0.433 | 0.335 | 0.784 | 0.922 | 0.293 | 0.790 | 0.702 | 0.609 |
| Gender | r-value | −0.141 | 1.000 | 0.217 | 0.081 | −0.292 | 0.027 | −0.259 | −0.545 | −0.249 | 0.182 | 0.095 |
| | p-value | 0.173 | | 0.036 | 0.530 | 0.017 | 0.807 | 0.017 | 0.000 | 0.023 | 0.106 | 0.395 |
| Age | r-value | 0.274 | 0.217 | 1.000 | 0.049 | 0.203 | 0.171 | −0.004 | −0.340 | −0.024 | 0.269 | 0.468 |
| | p-value | 0.008 | 0.036 | | 0.710 | 0.103 | 0.126 | 0.974 | 0.002 | 0.832 | 0.017 | 0.000 |
| Volume | r-value | −0.090 | 0.081 | 0.049 | 1.000 | 0.195 | 0.384 | 0.139 | −0.043 | 0.125 | −0.039 | 0.220 |
| | p-value | 0.488 | 0.530 | 0.710 | | 0.216 | 0.003 | 0.303 | 0.756 | 0.365 | 0.782 | 0.107 |
| ATP/Cr | r-value | 0.121 | −0.292 | 0.203 | 0.195 | 1.000 | 0.568 | 0.438 | 0.368 | 0.420 | −0.026 | 0.533 |
| | p-value | 0.335 | 0.017 | 0.103 | 0.216 | | 0.000 | 0.000 | 0.003 | 0.001 | 0.840 | 0.000 |
| ACh/Cr | r-value | 0.031 | 0.027 | 0.171 | 0.384 | 0.568 | 1.000 | 0.480 | 0.119 | 0.462 | 0.217 | 0.677 |
| | p-value | 0.784 | 0.807 | 0.126 | 0.003 | 0.000 | | 0.000 | 0.291 | 0.000 | 0.056 | 0.000 |
| NO/Cr | r-value | −0.011 | −0.259 | −0.004 | 0.139 | 0.438 | 0.480 | 1.000 | 0.292 | 1.000 | 0.071 | 0.434 |
| | p-value | 0.922 | 0.017 | 0.974 | 0.303 | 0.000 | 0.000 | | 0.007 | 0.000 | 0.532 | 0.000 |
| Nitrite/Cr | r-value | 0.116 | −0.545 | −0.340 | −0.043 | 0.368 | 0.119 | 0.292 | 1.000 | 0.290 | −0.308 | −0.062 |
| | p-value | 0.298 | 0.000 | 0.002 | 0.756 | 0.003 | 0.291 | 0.007 | | 0.008 | 0.006 | 0.587 |
| Nitrate/Cr | r-value | −0.030 | −0.249 | −0.024 | 0.125 | 0.420 | 0.462 | 1.000 | 0.290 | 1.000 | 0.038 | 0.415 |
| | p-value | 0.790 | 0.023 | 0.832 | 0.365 | 0.001 | 0.000 | 0.000 | 0.008 | | 0.744 | 0.000 |
| MCP-1/Cr | r-value | 0.043 | 0.182 | 0.269 | −0.039 | −0.026 | 0.217 | 0.071 | −0.308 | 0.038 | 1.000 | 0.311 |
| | p-value | 0.702 | 0.106 | 0.017 | 0.732 | 0.340 | 0.056 | 0.532 | 0.006 | 0.744 | | 0.006 |
| IL-5/_Cr | r-value | 0.057 | 0.095 | 0.468 | 0.220 | 0.533 | 0.677 | 0.434 | −0.062 | 0.415 | 0.311 | 1.000 |
| | p-value | 0.609 | 0.395 | 0.000 | 0.107 | 0.000 | 0.000 | 0.000 | 0.537 | 0.000 | 0.006 | |

Binary Logistic Regression

Based on the observed correlation test results, the discriminatory power of the independent variables, individually and in different combination models, in predicting someone being OAB symptomatic was assessed using binary logistic regression test (Table 4). When independent variables were tive accuracy (76.5%, the overall correctly specified group percentage) compared to the other two models (combination 1: 73.2%; combination 2: 67.9%), nevertheless, only 34 cases were included in this model (due to missing data for the independent variables) which decreases the reliability of the observed results. The following logistic model formulae were generated for combinations 1 and 3 based on the obtained constant and coefficients for these two models:

Combination 1

Age, ATP/Cr, ACh/Cr, Nitrite/Cr, MCP-1/Cr, IL-5/Cr

Logit($p$)=−1.738±1.404+4.985±2.914×age+ 3315.959±5435.254×[ATP]/[Cr]+(− 25204.194±20268.337)×[ACh]/[Cr]+ 26.799±32.967×[Nitrite]/[Cr]+6.755±25.132× [MCP-1]/[Cr]+(−61.838±148.740)×[IL-5]/[Cr]

The first parameter of the model (in bold) is a constant.

(i.e. OAB) equals $1/1+e^{-logit(p)}$. This value can be back-transformed to p (probability of being OAB) by the following formula:

$$(\text{predicted probability}) = \frac{1}{1 + e^{-logit(p)}},$$

where p ranges from 0 (OAB uncertain, i.e. very unlikely) to 1 (OAB certain).

TABLE 4

The discriminatory power of independent variables (i.e. gender, age, urine volume and urinary biomarkers) assessed by binary logistic regression.

| prediction model | n | P (H$_0$) | P (Model) | ΔP (%) | p-value | Coefficient±SE | Constant±SE |
|---|---|---|---|---|---|---|---|
| Gender | 95 | 62.1% | 62.1% | 0.0% | 0.171 | 0.600 ± 0.439 | 0.118 ± 0.344 |
| Age | 94 | 62.8% | 61.7% | −1.1% | 0.046 | 3.025 ± 1.518 | −0.806 ± 0.692 |
| volume | 62 | 64.5% | 64.5% | 0.0% | 0.744 | −3.416 ± 10.470 | 0.807 ± 0.697 |
| ATP/Cr | 66 | 59.1% | 59.1% | 0.0% | 0.759 | 119.010 ± 387.399 | 0.334 ± 0.273 |
| ACh/Cr | 83 | 57.8% | 57.8% | 0.0% | 0.937 | 663.187 ± 8415.748 | 0.302 ± 0.284 |
| NO/Cr | 85 | 58.8% | 58.8% | 0.0% | 0.776 | 1.521 ± 5.338 | 0.261 ± 0.400 |
| Nitrite/Cr | 83 | 59.0% | 59.0% | 0.0% | 0.286 | 16.950 ± 15.898 | 0.096 ± .330 |
| Nitrate/Cr | 83 | 59.0% | 59.0% | 0.0% | 0.553 | −4.705 ± 7.927 | 0.647 ± 0.527 |
| MCP-1/Cr | 80 | 58.8% | 58.8% | 0.0% | 0.355 | 13.030 ± 14.091 | 0.101 ± 0.347 |
| IL-5/Cr | 82 | 59.8% | 59.8% | 0.0% | 0.537 | 26.538 ± 43.026 | 0.303 ± 0.266 |
| Combination 1 | 56 | 60.7% | 73.2% | 12.5% | | | −1.738 ± 1.404 |
| Age | | | | | 0.087 | 4.985 ± 2.914 | |
| ATP/Cr | | | | | 0.542 | 3315.959 ± 5435.254 | |
| ACh/Cr | | | | | 0.214 | −25204.194 ± 20268.337 | |
| Nitrite/Cr | | | | | 0.416 | 26.799 ± 32.967 | |
| MCP-1/Cr | | | | | 0.788 | 6.755 ± 25.132 | |
| IL-5/Cr | | | | | 0.678 | −61.838 ± 148.740 | |
| Combination 2 | 56 | 60.7% | 67.9% | 7.2% | | | 0.448 ± 0.855 |
| ATP/Cr | | | | | 0.559 | 2299.391 ± 3934.772 | |
| ACh/Cr | | | | | 0.288 | −21685.723 ± 20402.344 | |
| NO/Cr | | | | | 0.638 | −6.014 ± 12.763 | |
| Nitrite/Cr | | | | | 0.762 | 8.585 ± 28.340 | |
| MCP-1/Cr | | | | | 0.383 | 19.906 ± 22.833 | |
| IL-5/Cr | | | | | 0.959 | 6.693 ± 130.940 | |
| Combination 3 | 34 | 64.7% | 76.5% | 11.8% | | | −6.396 ± 6.732 |
| Gender | | | | | 0.228 | 1.644 ± 1.363 | |
| Age | | | | | 0.249 | 14.812 ± 12.852 | |
| Volume | | | | | 0.782 | 8.625 ± 31.214 | |
| ATP/Cr | | | | | 0.675 | 1362.442 ± 3250.433 | |
| ACh/Cr | | | | | 0.813 | −8323.032 ± 35168.325 | |
| NO/Cr | | | | | 0.303 | −33.706 ± 32.720 | |
| Nitrite/Cr | | | | | 0.393 | 77.043 ± 90.269 | |
| MCP-1/Cr | | | | | 0.919 | −4.895 ± 48.360 | |
| IL-5/Cr | | | | | 0.989 | −2.759 ± 202.207 | | n = number of participants involved in the analysis based on available data; P(H$_0$): Null hypothesis prediction ability percentage; P(Model): Model prediction ability percentage; ΔP (%): percentage change in prediction ability; p-value: prediction ability of each individual variable involved in the model.

Combination 3

Gender, Age, Volume, ATP/Cr, ACh/Cr, NO/Cr, Nitrite/Cr, MCP-1/Cr, IL-5/Cr

Logit($p$)=−6.396±6.732+1.644±1.363×gender+ 14.812±12.852×age+8.625±31.214×volume+ 1362.442±3250.433×[ATP]/[Cr]+(− 8323.032±35168.325)×[ACh]/[Cr]+(− 33.706±32.720)×[NO]/[Cr]+77.043±90.269× [Nitrite]/[Cr]+(−4.895±48.360)[MCP-1]/[Cr]+(− 2.759±202.207)[IL-5]/[Cr]

The first parameter of the model (in bold) is a constant.

Values for each of the independent variables used in this equation should be range standardized to the following numbers before being placed in the formula: Age to 120 years old; ATP/Cr to 0.000001 mole/mg×dl$^{-1}$; ACh/Cr to 0.1 mole/mg×dl$^{-1}$; Nitrite to 200 nM/mg×dl$^{-1}$; MCP-1/Cr to 100 pg×ml$^{-1}$/mg×dl$^{-1}$; IL-5/Cr 100 pg×ml$^{-1}$/mg×dl$^{-1}$.

The outcome of the algorithm is a value of logit(p). For Logit(p)=y, the probability p of having a positive outcome ROC Curve Analysis The sensitivity and specificity (discriminatory power) of generated OAB prediction models were assessed via ROC curve analysis, results are illustrated in FIGS. 2A-2J, 3A-3C and Table 5. When the discriminatory of independent variables (urinary biomarkers and confounders) was assessed individually, none of the variables except Age (AUC=0.663 (+0.056)) exhibited a ROC curve line above the diagonal line (diagnostic test has no discriminative value). In contrast, all of the combination models had ROC curves above the diagonal line where combination 3 had the best discriminatory power (AUC=0.830 (+0.070), satisfactory OAB diagnostic test) and was followed by combination 1 (AUC=0.715 (+0.070), satisfactory OAB diagnostic test) and combination 2 (AUC=0.680 (+0.072), poor diagnostic test). In other words, combination 3 and 1 models have predictive ability to discriminate OAB symptomatic individuals from asymptomatics.

TABLE 5

Receiver operating characteristic curve results for OAB prediction models

| Prediction model | AUC (±SE) | P-value | 95% CI |
|---|---|---|---|
| Gender | 0.430 (±0.061) | 0.256 | 0.310-0.550 |
| Age | 0.663 (±.056) | 0.008 | 0.554-0.772 |
| Urine volume | 0.554 (±0.073) | 0.485 | 0.411-0.697 |
| ATP/Cr | 0.571 (±0.075) | 0.331 | 0.423-0.719 |
| ACh/Cr | 0.518 (±0.066) | 0.782 | 0.388-0.648 |
| NO/Cr | 0.506 (±0.064) | 0.922 | 0.381-0.631 |
| Nitrite/Cr | 0.568 (±0.067) | 0.295 | 0.437-0.699 |
| Nitrate/Cr | 0.517 (±0.065) | 0.788 | 0.390-0.645 |
| MCP-1/Cr | 0.525 (±0.066) | 0.699 | 0.397-0.654 |
| IL-5/Cr | 0.534 (±0.065) | 0.606 | 0.406-0.662 |
| Combination 1 | 0.715 (±0.070) | 0.007 | 0.579-0.852 |
| Combination 2 | 0.680 (±0.072) | 0.024 | 0.538-0.822 |
| Combination 3 | 0.830 (±0.070) | 0.002 | 0.693-0.966 |

AUC: area under curve; SE: standard error; CI: confidence interval.

DISCUSSION

In this study, cluster analysis was applied to categorize participants based on their reported profile of urinary symptoms and associated bothersome levels. So far, only few studies (e.g. Norman et al. 1994; Cinar et al. 2008; Hall et al. 2008) have applied this method for clustering participants based on their urological symptoms, where most of them involved participants with a broad range of urological symptoms rather focusing on a specific type of urological disease. To the best of the author's knowledge, this is the first study that has applied this technique for clustering participants based on their OAB symptoms. Both urinary symptoms and associated bothersome scores were incorporated in cluster analyses individually and in combination. In general, two clusters were identified for all the cluster analyses run based on different aspects of the ICIQ-OAB questionnaire data. Participants with acute UTI were excluded from the analysis in order to circumvent the effect of UTI on the manifestation of urinary symptoms similar to those of OAB (i.e. frequency symptom) and consequently on cluster analyses.

One of the most important advantages of the novel symptom-based clustering method was that 'urgency' was the main OAB predictor; whereas, in the current diagnostic method (i.e. total ICIQ-OAB≥7=OAB positive) none of the symptoms has superiority over others which leads to underestimation of the importance of the 'urgency' symptom in OAB diagnosis. Overall, these findings prompt re-examination of the current OAB diagnostic classification with the aim of diagnosing OAB patients at a much earlier stage of its development.

Given unsatisfactory treatment outcomes for OAB, it may be that developed OAB is only partially reversible; therefore, the advantage of detecting OAB at earlier stages of its progress based on the urinary symptom criteria developed in this study offers a significant opportunity to improve treatment outcome. In addition, the issue of overlap in biomarker expression between "OAB symptomatic" and "asymptomatic" groups suggests that any one biomarker will be inadequate to accurately identify OAB and that a panel of biomarkers may be required to provide satisfactory sensitivity and specificity. This hypothesis was supported when the predictability power of these biomarkers was assessed using logistic regression analysis, where in general combination of biomarkers (with or without confounders) had higher OAB predictability power. The potential biomarkers did not independently show the ability to discriminate between the two clusters; however, the discriminatory accuracy of biomarkers were substantially improved when they were combined and the highest satisfactory accuracy (i.e. sensitivity and specificity) figures were seen with combination 1 (AUC=0.715 (±0.070), fair OAB diagnostic test) and combination 3 (AUC=0.830 (±0.070), good OAB diagnostic test) models. This further supports the hypothesis that a panel of biomarkers may be more imperative to consider than each biomarker's independent performance in the development of novel OAB biomarker-based diagnostic tools. The combination of urine-based biomarkers provides a very high level of sensitivity and specificity for OAB; where two of the generated combination sets reached the satisfactory clinical accuracy of above>70%; far exceeding the accuracy of current 'gold-standard' methods for diagnosis.

Conclusion: The developed panel of OAB biomarkers further provides basis for the early and more accurate detection of OAB which may not only improve treatment outcomes but may allow clinicians to monitor stage-specific responses to OAB treatments.

REFERENCES

Abrams P, Avery K, Gardener N, Donovan J. The International Consultation on Incontinence Modular Questionnaire: www.iciq.net. The Journal of Urology. 2006; 175(3 Pt 1):1063-6

Cinar A, Hall S A, Link C L, Kaplan S A, Kopp Z S, Roehrborn C G, et al. Cluster analysis and lower urinary tract symptoms in men: findings from the Boston Area Community Health Survey. BJU International. 2008; 101 (10):1247-56.

Hall S A, Cinar A, Link C L, Kopp Z S, Roehrborn C G, Kaplan S A, et al. Do urological symptoms cluster among women? Results from the Boston Area Community Health Survey. BJU International. 2008; 101(10):1257-66.

Norman R W, Nickel J C, Fish D, Pickett S N. 'Prostate-related symptoms' in Canadian men 50 years of age or older: prevalence and relationships among symptoms. British Journal of Urology. 1994; 74(5):542-50.

Norusis M J. SPSS 16.0 Statistical Procedures Companion, Chapter 16 [Internet]. 2008 [cited 4 Jun. 16]. Available from: http://www.norusis.com/book SPC v16.php

The invention claimed is:

1. A method comprising:

measuring the concentrations of adenosine triphosphate (ATP), acetylcholine (ACh), nitrite, monocyte chemoattractant protein 1 (MCP-1), nitric oxide (NO), and interleukin 5 (IL-5) in a sample obtained from a subject;

normalising the concentrations to the concentration of creatinine (Cr) in the sample;

range standardising the normalised concentrations and subject's age to the following values: Age to 120 years old; ATP/Cr to 0.000001 mole/(mg×(dl$^{-1}$)); ACh/Cr to 0.1 mole/(mg×(dl$^{-1}$)); —NO/Cr to 20,000 nM/(mg× (dl$^{-1}$)); Nitrite to 200 nM/(mg×(dl$^{-1}$)); MCP-1/Cr to 100 (pg×(ml$^{-1}$))/(mg×(dl$^{-1}$)); IL-5/Cr 100 (pg×(ml$^{-1}$))/ (mg×(dl$^{-1}$));

applying the normalised and range standardised concentrations to either of the following formulas:

Logit($p$)=−1.738+1.404+4.985+2.914×subject's age+ 3315.959+5435.254×[ATP]/[Cr]+(−25204.194− 20268.337)×[ACh]/[Cr]+26.799±32.967×[nitrite]/[Cr]+6.755±25.132[MCP-1]/[Cr]+(− 61.838=148.740)[IL-5]/[Cr], or Logit($p$)=−6.396+6.732+1.664=1.363×gender+ 14.812+12.852×subject's age+8.625+31.214×volume+1362.442+3250.433×[ATP]/[Cr]+(−8323032+35168.325)×[ACh]/[Cr]+(−33.706+ 32.720)×[NO]/[Cr]+77.043+90.269×[nitrite]/[Cr]+(−4.895+48.360)[MCP-1]/[Cr]+(−2.759+ 202.207)[IL-5]/[Cr];

and calculating Logit;

wherein a Logit value above a predetermined threshold indicates that the subject has OAB.

2. The method of claim 1, further comprising calculating the predicted probability of the subject having OAB using the following formula: (predicted probability)=1/(1+e^logit (p)), wherein a probability of 1 indicates that the subject has OAB and a probability of 0 indicates that the subject does not have OAB.

3. The method of claim 1, wherein the sample is a urine sample.

4. The method of claim 1, wherein the concentrations of any of ATP, ACh, nitrite, MCP-1, NO, IL-5 or Cr are measured using an antibody-based platform or an RNA aptamer-based platform or a combination thereof.

5. The method of claim 1, wherein the method further comprises administering a therapeutic agent to a subject diagnosed as having OAB.

6. The method of claim 5, wherein the therapeutic agent is an antimuscarinic drug or a β3 adrenergic receptor agonist.

7. The method of claim 6, wherein the antimuscarinic drug is selected from one or more of darifenacin, oxybutynin, tolterodine, solifenacin, trospium, flavoxate, propiverine or fesoterodine.

8. The method of claim 6, wherein the β3 adrenergic receptor agonist is mirabegron.

9. A method of monitoring the progression of OAB, the method comprising measuring first and second Logit values according to the method of claim 1, wherein the first and second Logit values are obtained from first and second samples obtained from a subject having or suspected of having OAB.

10. The method of claim 9, wherein the first and second samples are obtained at an interval of at least two weeks.

11. A kit comprising binding molecules that specifically bind to adenosine triphosphate (ATP), acetylcholine (ACh), nitrite, monocyte chemoattractant protein 1 (MCP-1), interleukin 5 (IL-5) and creatinine (Cr).

12. The kit according to claim 11, wherein the binding molecules are antibodies.

* * * * *